United States Patent
Epstein et al.

(10) Patent No.: US 10,682,511 B2
(45) Date of Patent: Jun. 16, 2020

(54) DEFIBRILLATOR FOR MINIMALLY INVASIVE SURGICAL PROCEDURES

(71) Applicants: Stephen T. Epstein, Hatboro, PA (US); John J. Sinisi, Warminster, PA (US)

(72) Inventors: Stephen T. Epstein, Hatboro, PA (US); John J. Sinisi, Warminster, PA (US)

( * ) Notice: Subject to any disclaimer, the term of this patent is extended or adjusted under 35 U.S.C. 154(b) by 217 days.

(21) Appl. No.: 15/230,231

(22) Filed: Aug. 5, 2016

(65) Prior Publication Data

US 2018/0036528 A1 Feb. 8, 2018

(51) Int. Cl.
*A61N 1/05* (2006.01)
*A61N 1/39* (2006.01)

(52) U.S. Cl.
CPC ......... *A61N 1/0587* (2013.01); *A61N 1/0595* (2013.01); *A61N 1/39* (2013.01); *A61N 1/0563* (2013.01)

(58) Field of Classification Search
CPC ......... A61N 1/046; A61N 1/0587; A61N 1/39
See application file for complete search history.

(56) References Cited

U.S. PATENT DOCUMENTS

| | | | | |
|---|---|---|---|---|
| 2,985,172 A | * | 5/1961 | Jones | A61N 1/0587 607/119 |
| 3,389,703 A | * | 6/1968 | Criswell | A61N 1/04 607/119 |
| 3,670,736 A | | 6/1972 | Panico | |
| 4,554,910 A | | 11/1985 | Lally | |
| 4,681,112 A | | 7/1987 | Jones et al. | |
| 4,705,044 A | | 11/1987 | Deluhery et al. | |
| 4,852,585 A | | 8/1989 | Heath | |
| 5,645,522 A | | 7/1997 | Lurie et al. | |
| 5,904,711 A | | 5/1999 | Flom et al. | |
| 6,097,987 A | | 8/2000 | Milani | |
| 6,156,060 A | * | 12/2000 | Roy | A61N 1/403 128/898 |
| 6,360,125 B1 | | 3/2002 | Weil et al. | |
| 6,721,597 B1 | | 4/2004 | Bardy et al. | |
| 6,950,705 B2 | | 9/2005 | Bardy et al. | |
| 6,961,611 B2 | | 11/2005 | Dupelle | |
| 6,969,259 B2 | | 11/2005 | Pastrick et al. | |
| 7,016,727 B2 | | 3/2006 | Powers et al. | |
| 7,245,974 B2 | | 7/2007 | Dupelle et al. | |
| 7,274,962 B2 | | 9/2007 | Bardy et al. | |

(Continued)

FOREIGN PATENT DOCUMENTS

EP 353341 A1 2/1990

*Primary Examiner* — Eric D. Bertram
(74) *Attorney, Agent, or Firm* — Lamorte & Associates P.C.

(57) ABSTRACT

A defibrillation system with a unique paddle assembly. The paddle assembly has a paddle head with a conductive surface. The paddle head is introduced into the chest through a small surgical incision. The paddle head is connected to a handle by an elongated shaft. The elongated shaft has an electrically conductive core that is covered in a dielectric insulator. The elongated shaft is malleable. A pivot connection joins one end of the elongated shaft to the paddle head. The pivot connection enables the paddle head to move through a range of different orientations with respect to the elongated shaft. Electricity passes through the conductive core of the elongated shaft and into the paddle head.

17 Claims, 7 Drawing Sheets

(56) References Cited

U.S. PATENT DOCUMENTS

| | | | |
|---|---|---|---|
| 8,452,393 B1* | 5/2013 | Epstein | A61N 1/046 607/142 |
| 2002/0042629 A1 | 4/2002 | Bardy et al. | |
| 2002/0062144 A1 | 5/2002 | Zadini et al. | |
| 2002/0103510 A1 | 8/2002 | Bardy et al. | |
| 2002/0107548 A1 | 8/2002 | Bardy et al. | |
| 2003/0045905 A1 | 3/2003 | Daynes et al. | |
| 2003/0078470 A1 | 4/2003 | Borst et al. | |
| 2003/0191501 A1 | 10/2003 | Miller et al. | |
| 2004/0088035 A1 | 5/2004 | Guenst et al. | |
| 2004/0162588 A1 | 8/2004 | Watanabe et al. | |
| 2004/0172071 A1 | 9/2004 | Bardy et al. | |
| 2004/0186545 A1 | 9/2004 | Rosero et al. | |
| 2004/0199236 A1 | 10/2004 | Laske et al. | |
| 2004/0210259 A1 | 10/2004 | Rock et al. | |
| 2004/0230231 A1 | 11/2004 | Thacker et al. | |
| 2005/0119705 A9 | 6/2005 | Bardy et al. | |
| 2005/0192639 A1 | 9/2005 | Bardy et al. | |
| 2005/0240232 A9 | 10/2005 | Bardy et al. | |
| 2006/0004416 A1 | 1/2006 | Bardy et al. | |
| 2006/0025826 A1 | 2/2006 | Erlinger et al. | |
| 2006/0155337 A1 | 7/2006 | Bardy et al. | |
| 2006/0259081 A1 | 11/2006 | Vaisnys et al. | |
| 2007/0233197 A1 | 10/2007 | Jung et al. | |
| 2007/0299473 A1 | 12/2007 | Matos | |
| 2008/0033495 A1 | 2/2008 | Kumar | |
| 2011/0009936 A1 | 1/2011 | Satake et al. | |
| 2014/0194965 A1 | 7/2014 | Osypka | |

* cited by examiner

DEFIBRILLATOR FOR MINIMALLY INVASIVE SURGICAL PROCEDURES

BACKGROUND OF THE INVENTION

1. Field of the Invention

In general, the present invention relates to defibrillation paddles. More particularly, the present invention relates to defibrillation paddles that are used during minimally invasive procedures wherein the defibrillation paddle is brought into direct contact with the tissue of the heart.

2. Prior Art Description

It is known that a heart muscle that has stopped beating or is beating erratically can sometimes be caused to beat normally by passing an electrical current through the tissue of the heart. The science of applying an electrical current to the heart is known as defibrillation and has been evolving for many years.

Defibrillators are devices that are specifically designed to pass an electrical current into a patient's heart. In the field of defibrillators, there are non-intrusive defibrillators and intrusive defibrillators. Non-intrusive defibrillators have electrodes that attach to the skin of a patient. The non-intrusive defibrillators pass electricity through the body from one external point to another. Such non-intrusive defibrillators are used by rescue workers, paramedics and the like to revive a person whose heart has stopped. Since non-intrusive defibrillators pass electricity through the body, hoping to affect the heart, large electrical charges are used. These charges often cause the skin of the patient to burn at the areas where the defibrillator is attached to the body and where electricity passes into and out of the patient's body.

Intrusive defibrillators are used by physicians primarily in the operating room of hospitals. During many surgical procedures, a patient's heart may be temporarily stopped. In such situations, the patient's blood flow is transferred to an external pump. Once the surgical procedure is complete, a defibrillator is commonly used to restart the heart. When the heart muscle itself is exposed, the paddle terminals of the defibrillator are touched directly to the heart muscle. A small jolt of electricity is then passed through the tissue of the heart muscle to restart the heart's beat. Since the electricity is being applied directly to the heart muscle, low currents of electricity are used. However, even these low currents of electricity can result in some heart muscle tissue becoming burned in the areas of contact with the defibrillator's paddles, especially if there is not good contact with the heart tissue.

One way to reduce the potential of damage to the heart muscle is to use a defibrillation system that touches the heart with only a single paddle. If only one paddle touches the heart, it is easier for a physician to bring that single paddle into proper contact with the heart.

In the prior art, defibrillator systems have been made that use only one paddle. In such systems, a patient is laid upon a conductive pad. A single paddle is provided. Both the single paddle and the conductive pad are connected to the defibrillator. The single paddle is then touched to the tissue of the heart. Electricity passes through the heart, through the back of the body and to the conductive pad. Since only one paddle is used, the chances that one paddle will be poorly positioned is reduced by half, as compared to two paddle systems. Such prior art defibrillation systems are exemplified by Japanese Reference No. JP2001121885, entitled Defibrillating Electrode And Defibrillation System and U.S. Pat. No. 8,452,393 to Epstein, entitled Defibrillation Paddle Structure And Its Associated Method Of Use.

When surgery is performed on the heart, that surgery can often be defined as either open heart surgery or minimally invasive surgery. During open heart surgery, the ribcage is opened at the sternum by the surgeon to expose the heart. This type of surgery requires a long and painful recovery period as the ribcage heals. As surgical procedures evolve, an increasing number of surgical procedures on the heart are being performed using minimally invasive techniques. When minimally invasive surgical techniques are used, the ribcage remains largely undisturbed. Small entrance holes are formed between the ribs of the ribcage that enable elongated surgical instruments to be advanced toward the heart in the chest cavity. However, this presents certain problems, especially when it comes to defibrillators.

When the paddle head of a defibrillator contacts the muscle tissue of the heart, the largest contact area possible is desired. If only a small contact area exists, all of the electrical current passing into the heart is forced to pass through the small area of tissue in contact with the defibrillator paddle head. This concentrates the electricity and can cause tissue burning and damage to the heart tissue. A large area of contact is desired because it distributes the flow of electrical current and is, therefore, less likely to cause burning. The key to avoiding tissue damage made by a defibrillator paddle is to have uniform contact between the paddle and the tissue of the heart muscle. To further complicate matters, a physician may decide to shock the heart at a specific spot. That location may be on the top of the heart or along one of the sides of the heart. The doctor must maneuver the defibrillator paddle to that portion of the heart while still maintaining a flush contact between the defibrillator paddle and the tissue of the heart. If there is not a flush contact, the odds greatly increase that the defibrillator paddle may cause an electrical burn. Furthermore, without a flush contact, the defibrillator may fail to affect the heart muscle in the desired manner.

A further problem exists because, in order to use a defibrillation paddle in a minimally invasive surgical technique, the paddle head has to be small enough to pass through one of the access openings made between the ribs. However, the paddle must also not be so small that it can burn heart tissue when in use.

A need therefore exists for an improved defibrillator paddle design, wherein the orientation between the contact surface of the paddle and the handle of the paddle can be selectively adjusted. In this manner, the paddle can be oriented to the needs of the physician, thereby making the defibrillator paddle less dangerous and more effective. A need also exists for an improved defibrillator design where the paddle head is small enough to be used during minimally evasive surgical procedure, yet is large enough to safely disperse the electrical current along the tissue of the heart. These needs are met by the present invention as described and claimed below.

SUMMARY OF THE INVENTION

The present invention is a defibrillation system with a unique paddle assembly. The paddle assembly has a dielectric handle. The paddle assembly also has a paddle head with a conductive surface. The paddle head is introduced into the chest through a small surgical incision. The paddle head is manipulated until the conductive surface makes flush contact with the tissue of the heart.

The paddle head is connected to the handle by an elongated shaft. The elongated shaft has an electrically conductive core that is covered in a dielectric insulator. The elongated shaft is malleable. This enables the elongated shaft to be configurable into different shapes by manual manipulation.

A pivot connection joins one end of the elongated shaft to the paddle head. The pivot connection enables the paddle head to move through a range of different orientations with respect to the elongated shaft. The pivot connection also provides an electrical interconnection between the conductive core of the elongated shaft and the conductive surface of the paddle head.

As electricity passes through the paddle assembly, the electricity passes through the conductive core of the elongated shaft and into the paddle head. This configuration enables both the elongated shaft and the paddle head to be made very narrow. As such, the overall system is well adapted for use with minimally invasive procedures, where only small incisions are made into a patient's body.

BRIEF DESCRIPTION OF THE DRAWINGS

For a better understanding of the present invention, reference is made to the following description of exemplary embodiments thereof, considered in conjunction with the accompanying drawings, in which.

DETAILED DESCRIPTION OF THE DRAWINGS

Although the present invention defibrillator can be embodied in many ways, the embodiment illustrated shows only two possible defibrillator designs. These embodiments are selected in order to set forth the best modes contemplated for the invention. The illustrated embodiments, however, are merely exemplary and should not be considered a limitation when interpreting the scope of the appended claims.

Figure 1:
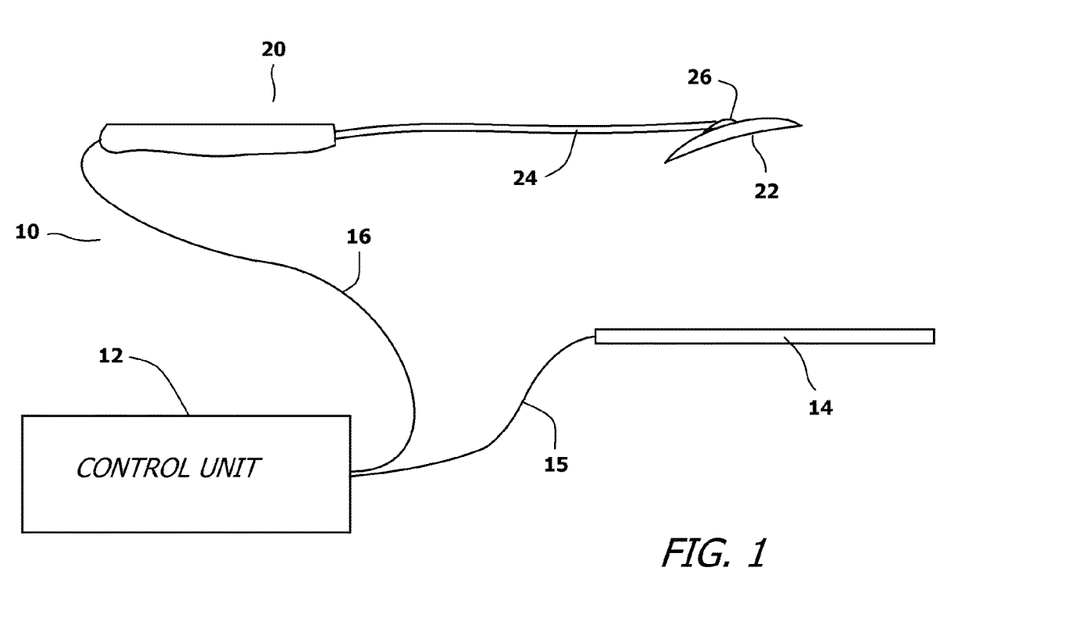
FIG. 1 shows an exemplary embodiment of a defibrillation system.

Referring to FIG. 1, there is shown an exemplary embodiment of a defibrillation system 10 in accordance with the present invention. The defibrillation system 10 consists of a control unit 12 that controls the electrical current and waveform that will be passed through the heart muscle. The control unit 12 has adjustable controls and safeguards typical in the industry. There are several defibrillator systems that are commercially available, the control unit of most any prior art defibrillator systems can be adapted for use as part of the present invention defibrillation system.

A conductive pad 14 is provided. The conductive pad 14 is connected to the control unit 12 by a first flexible terminal wire 15. A paddle assembly 20 is also attached to the control unit 12 by a second flexible terminal wire 16. The paddle assembly 20 has a conductive contact surface 22. The control unit 12 creates an electrical bias between the conductive contact surface 22 of the paddle assembly 20 and the conductive pad 14. Accordingly, when both the conductive pad 14 and the conductive contact surface 22 of the paddle assembly 20 are touched to a patient, electricity can flow through the patient between these surfaces. In common use, a patient would be placed atop the conductive pad 14. The paddle assembly 20 would be manipulated by a surgeon inside the body so that the conductive contact surface 22 touches heart tissue. The defibrillator system 10 is then activated so that an electrical current will pass through the heart and the portion of the body between the conductive contact surface 22 and the conductive pad 14.

The conductive contact surface 22 is supported by the structure of a paddle head 26. The features of the paddle head 26 are later explained in greater detail. The paddle head 26 is set upon a malleable shaft 24. The malleable shaft 24 attaches the paddle head 26 to a handle 28. The handle 28 is ergonomically shaped to fit comfortably in a physician's hand. The physician using the paddle assembly 20 holds the paddle assembly 20 by grasping the handle 28.

Figure 2:
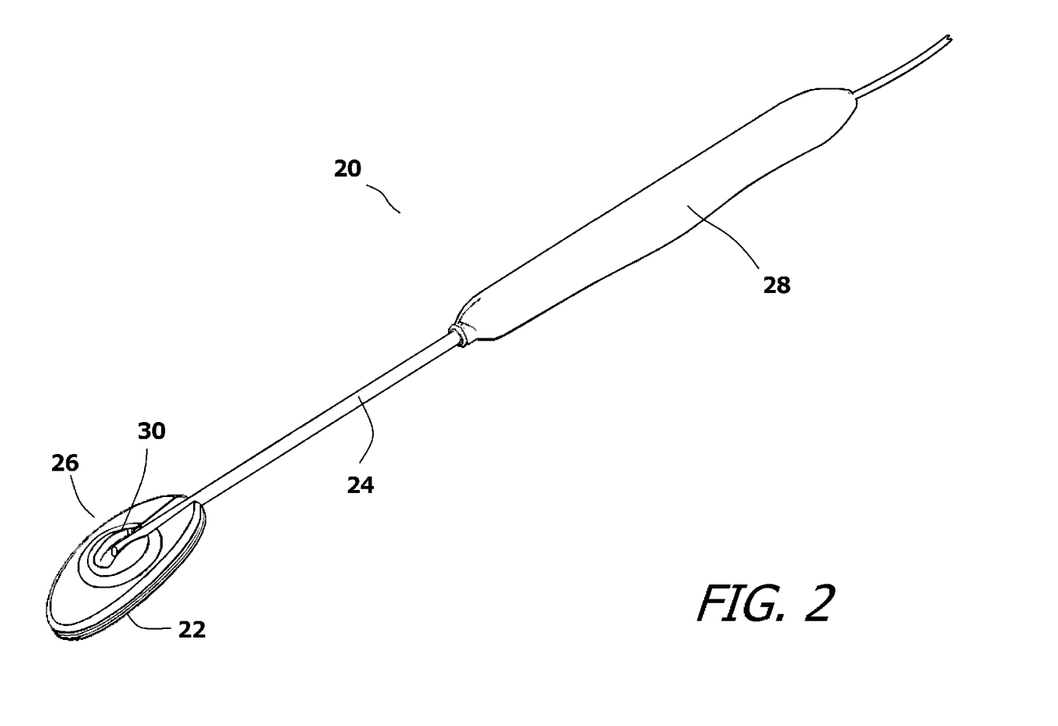
FIG. 2 is an enlarged perspective view of the paddle assembly used in the system of FIG. 1.
Figure 3:
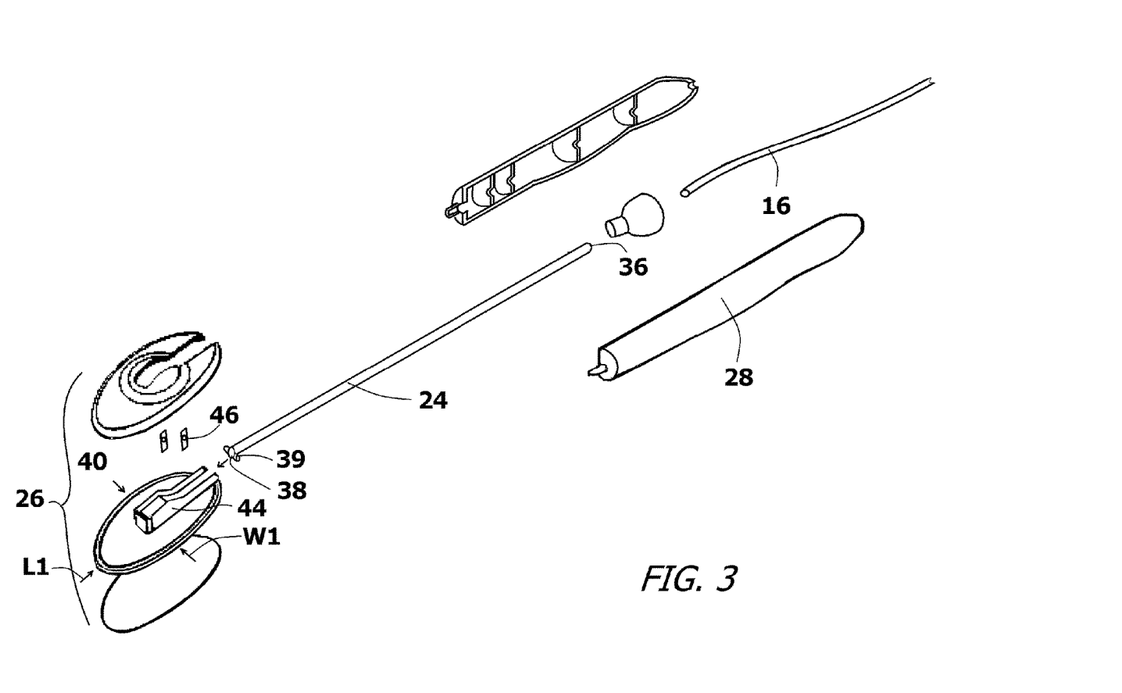
FIG. 3 is an exploded view of the paddle assembly of FIG. 2.

Referring to FIG. 2 and FIG. 3 in conjunction with FIG. 1, it can be seen that the paddle head 26 is attached to the malleable shaft 24 at a pivot joint 30. This enables the orientation of the paddle head 26 to be selectively altered relative the malleable shaft 24. The pivot joint 30 enables the orientation of the paddle head 26 to be altered. However, the paddle head 26 must be manually moved with a concerted effort. The pivot joint 30 is not so loose that gravity or slight contact alters the orientation of the paddle head 26. As such, the paddle head 26 remains in the orientation it is placed as it is advanced into the body and brought into contact with the heart.

Likewise, the malleable shaft 24 can be manually altered into different shapes and curvatures using a concerted manual effort. The malleable shaft 24 can be bent. However, the malleable shaft 24 is relatively stiff. As such, any bend or curvature purposely set into the malleable shaft 24 will remain in the malleable shaft 24 as the shaft is inserted into the body to contact the heart. In this manner, a physician using the paddle assembly 20 can selectively change the orientation of the paddle head 26 and the conductive contact surface 22 so that the conductive contact surface 22 abuts flush against the heart muscle at a position most advantageous by the surgeon during the operation.

Figure 4:
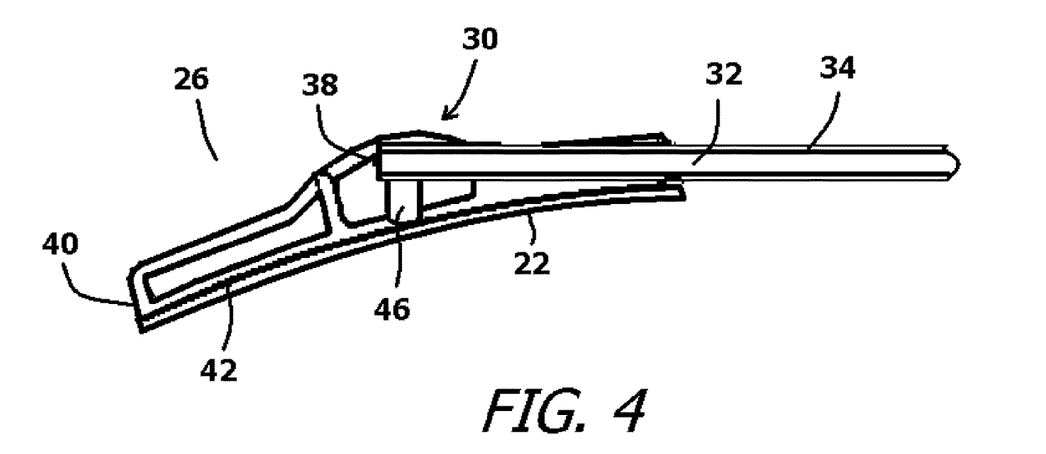
FIG. 4 is an enlarged cross-sectional view of the paddle head component of the exemplary defibrillation system.

Referring to FIG. 4 in conjunction with FIG. 3, it can be seen that malleable shaft 24 has a conductive core 32 that is surrounded by a dielectric insulator 34. In this manner, electricity can travel through the malleable shaft 24 from one end to the other. However, electricity cannot pass out of, or into, the malleable shaft 24 at any points other than the ends. The first end 36 of the malleable shaft 24 extends into the handle 28. The handle 28 is dielectric. Inside the confines of the handle 28, the first end 36 of the malleable shaft 24 is soldered, or otherwise electrically connected, to the second flexible terminal wire 16 that leads to the control unit 12 (FIG. 1).

The opposite second end 38 of the malleable shaft 24 connects to the paddle head 26 at the pivot joint 30. Two pivot nubs 39 extend from the second end 38 of the malleable shaft 24. The pivot nubs 39 are conductive and are coupled to the conductive core 32 of the malleable shaft 24. The paddle head 26 swings about the pivot nubs 39.

The paddle head 26 can have different shapes depending upon the size of the patient and the procedure being performed. For a minimally invasive procedure, where the paddle head 26 is being inserted through a small incision, the paddle head 26 is preferably oblong in shape, such as a rectangle or an oval. As is shown, the paddle head 26 has a maximum width W1, which is preferably less than 50 millimeters. The paddle head 26 has a length L1, which is preferably about twice as long as the width W1. As such, the maximum length is preferably less than 100 millimeters. The paddle head 26 has a thin dielectric body 40. The body 40 is preferably made of a flexible but resilient material. In this manner, the width W1 of the paddle head 26 can be made momentarily smaller by being manually compressed. This helps a physician insert the paddle head 26 through small incisions and to pass the paddle head 26 between the ribs of a patient.

The body 40 of the paddle head 26 has a curved face 42. The curved face 42 is either coated with, or covered by, the conductive contact surface 22. A connection hub 44 is disposed on the side of the body 40 opposite the conductive contact surface 22. The connection hub 44 forms part of the pivot joint 30 and is shaped as a yoke that receives the pivot nubs 39 at the second end 38 of the malleable shaft 24. At least one conductive lead 46 extends from the connection hub 44 to the conductive contact surface 22 at the opposite side of the body 40. In this manner, when the malleable shaft 24 is engaged with the connection hub 44, a reliable electrical connection exists between the conductive contact surface 22 and the conductive core 32 of the malleable shaft 24. Accordingly, any current passing through the conductive core 32 of the malleable shaft 24 can flow into the conductive contact surface 22 on the curved face surface 42 of the body 40. The electrical contact remains regardless of the angle of orientation achieved between the malleable shaft 24 and the paddle head 26 at the pivot joint 30.

Current is introduced into the conductive core 32 of the malleable shaft 24 at the opposite first end 36 of the malleable shaft 24. The first end 36 of the malleable shaft 24 passes into the dielectric handle 28. Inside of the handle 28, the conductive core 32 of the malleable shaft 24 is exposed and is soldered to the second flexible terminal wire 16. The second flexible terminal wire 16 extends back to the control unit 12 of the defibrillation system 10. In operation, the paddle head 26 passes into the chest cavity through a small incision made by a physician. The paddle head 26 is positioned about the heart so that the paddle head 26 touches the tissue of the heart in a location selected by the physician. The physician shapes the malleable shaft 24 and manipulates the handle 28 in such a manner as to maximize the contact area between the conductive contact surface 22 on the paddle head 26 and the tissue of the heart. Once in the proper position and in maximum contact, the defibrillation system 10 is activated. Electrical current passes through the first flexible terminal wire and into the conductive core 32 of the malleable shaft 24. The electricity continues through the malleable shaft 24 and passes into the conductive leads 46 at the pivot joint 30. The leads 46 conduct the current to the conductive contact surface 22 that is in contact with the heart tissue. The current passes into the heart so as to affect the heart. The current passes though the heart and into the body tissue between the heart and the conductive pad 14. The circuit is complete when the current passes out of the patient's body and into the conductive pad 14 (FIG. 1), wherein the current returns to the control unit 12 (FIG. 1). Since the contact area with the heart is large and the body contact with the conductive pad 14 is large, the passing current is dispersed and no burn injuries occur.

Figure 5:
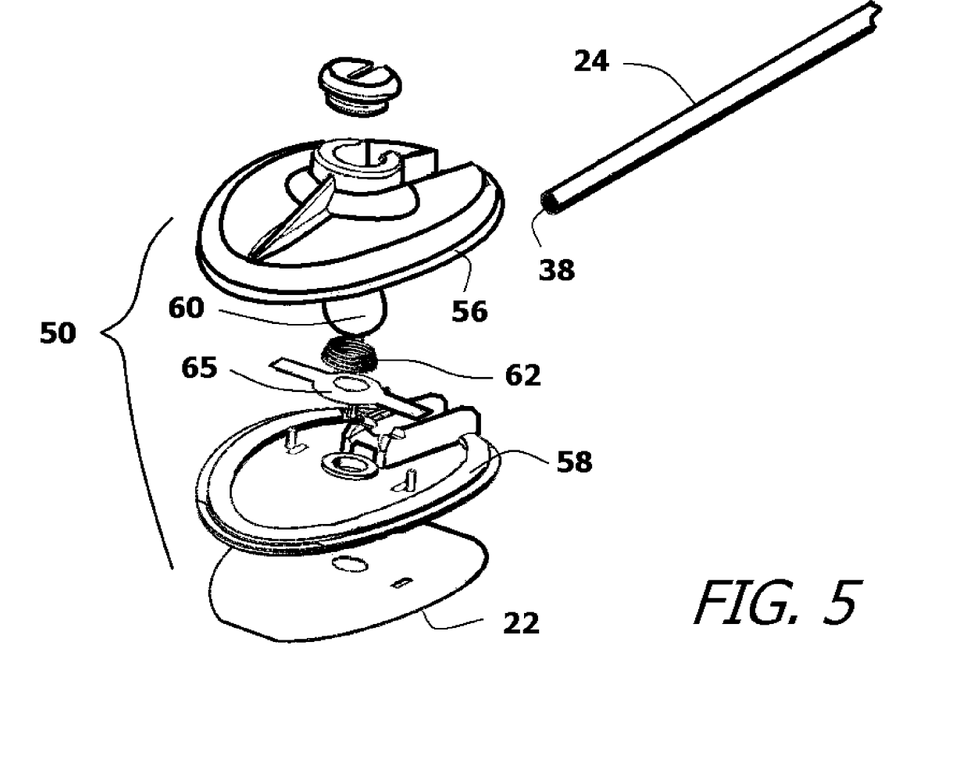
FIG. 5 is an exploded view of an alternate embodiment of the paddle head.
Figure 6:
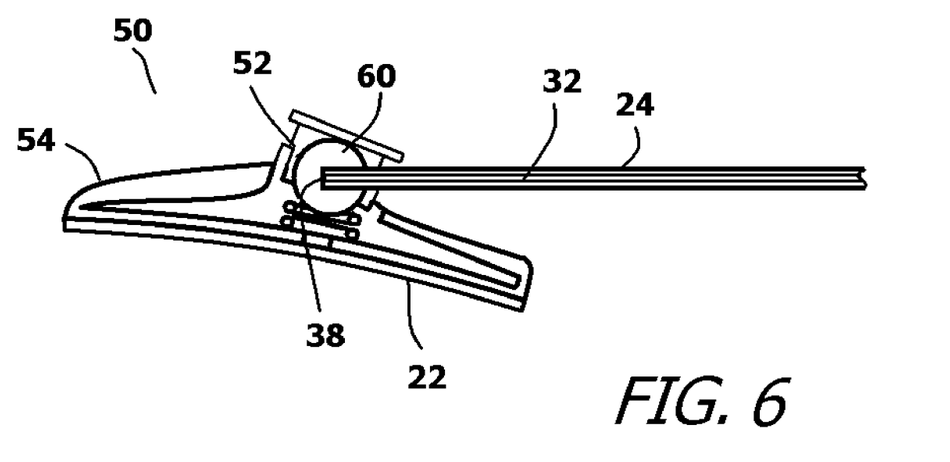
FIG. 6 is a cross-sectional view of the paddle head shown in FIG. 5.

Referring to FIG. 5 and FIG. 6, an alternate embodiment of the paddle head 50 is shown. The paddle head 50 is disposed at the end of a malleable shaft 24. The malleable shaft 24 is supported by a handle (not shown. The handle is the same as was previously described. The malleable shaft 24 is also the same as was previously explained with the exception that the second end 38 of the malleable shaft 24 is now shaped to engage a ball and socket joint 52.

In this embodiment, the body 54 of the paddle head 50 has an upper part 56 and a lower part 58. Interposed between the upper part 56 and the lower part 58 is a conductive ball bearing 60. A bore is formed in the ball bearing 60 that receives the second end 38 of the malleable shaft 24. The ball bearing 60 contacts the conductive core 32 of the malleable shaft 24 and therefore has the same electrical potential as does the conductive core 32 of the malleable shaft 24. The upper part 56 and the lower part 58 of the body 40 form a socket in which the ball bearing 60 sets. As such, the ball and socket joint 52 is formed. The ball and socket joint 52 enables the malleable shaft 24 to move relative the paddle head 50 with more degrees of freedom than are possible with the original embodiment that was previously described.

Inside the paddle head 50, the ball bearing 60 rests upon a spring 62. The spring 62 rests upon a contact 65 that has extensions that passes through the lower part 58 of the paddle head 50 and touches the conductive contact surface 22 on the face of the paddle head 50. In this manner, any electricity that flows into the malleable shaft 24 will pass through the conductive core 32 of the malleable shaft 24 and will pass into the ball bearing 60. The electricity then passes through the ball bearing 60 and into the spring 62 under the ball bearing 60. The spring 62 transfers the electricity to the conductive contact surface 22 on the paddle head 50.

Figure 7:
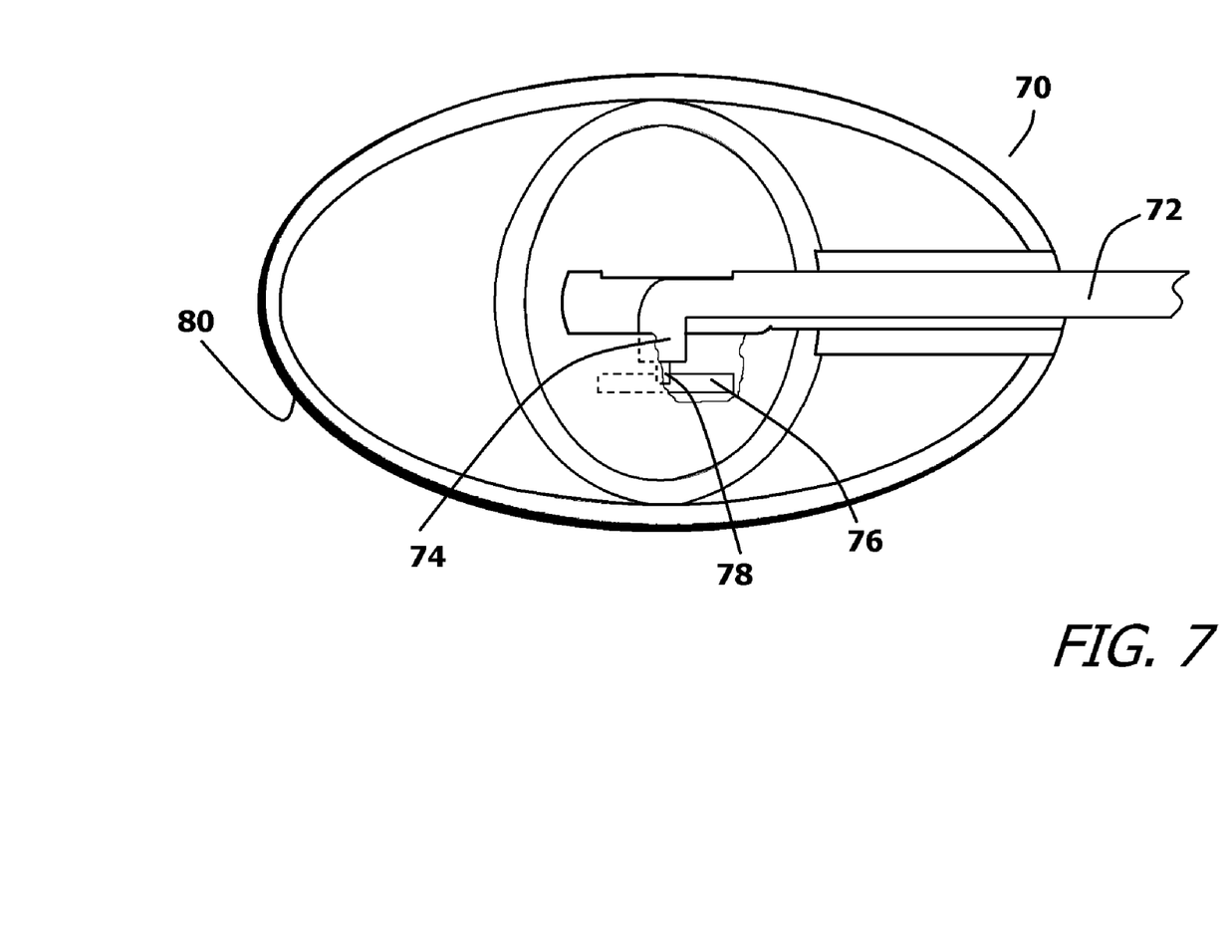
FIG. 7 is an enlarged partially fragmented view of an alternate paddle head component construction.

Referring to FIG. 7, an alternate embodiment of the paddle head 70 is shown. The paddle head 70 is disposed at the end of a malleable shaft 72. The malleable shaft 72 is supported by a handle (not shown. The handle is the same as was previously described. The malleable shaft 72 is also the same as was previously explained with the exception that the end of the malleable shaft 72 is now shaped is bent into an L-shaped engage. This produces a short lateral leg 74 at the end of the malleable shaft 72.

The short leg 74 is used as an axle around which the paddle head 70 can pivot. The resulting pivot joint enables the malleable shaft 72 to move relative the paddle head 70.

Inside the paddle head 70, the conductive core 76 of the malleable shaft 72 is exposed and is electrically coupled to an extension 78. The extension 78 passes through the paddle head 70 and touches the conductive contact surface 80 on the face of the paddle head 70. In this manner, any electricity that flows into the malleable shaft 72 will pass through the conductive core 76 of the malleable shaft 73 and will pass to the conductive contact surface 80 under the paddle head 70.

It will be understood that the embodiments of the present invention that are illustrated and described are merely exemplary and that a person skilled in the art can make many variations to those embodiments. For instance, the shape of the paddle head can be altered for different patients and different needs. The length of the malleable shaft can be altered. Likewise, the handle can have many shapes. All such embodiments are intended to be included within the scope of the present invention as defined by the claims.

What is claimed is:
1. A defibrillator assembly, comprising:
 a control unit having a first terminal wire and a second terminal wire, wherein said control unit creates an electrical bias between said first terminal wire and said second terminal wire;

a conductive pad that is electrically interconnected with said control unit by said first terminal wire;
a paddle having a dielectric handle, a paddle head, and an elongated shaft, wherein said paddle head has a conductive surface thereon;
wherein said elongated shaft joins said handle to said paddle head, said elongated shaft having a conductive core protected by external insulation, wherein said conductive core is connected to said second terminal wire within said handle; and
a pivot connection that joins said elongated shaft to said paddle head and enables said paddle head to move through a range of different orientations with respect to said elongated shaft, wherein said pivot connection creates an electrical interconnection between said conductive core of said elongated shaft and said conductive surface of said paddle head.

2. The assembly according to claim 1, wherein said paddle head has an oblong shape with a width and a length that is at least twice as long as said width.

3. The assembly according to claim 1, wherein said conductive surface on said paddle head is curved.

4. The assembly according to claim 1, further including at least one conductive element that extends through said paddle head from said conductive surface to said pivot connection, therein providing an electrical pathway from said pivot connection to said conductive surface.

5. The assembly according to claim 1, further including pivot nubs extending from said elongated shaft, wherein said pivot connection engages said pivot nubs and enables said paddle assembly to rotate about said pivot nubs through a range of motion.

6. The assembly according to claim 1, wherein said pivot connection is a ball joint having a conductive ball that is coupled to said elongated shaft.

7. The assembly according to claim 6, wherein an electrical pathway exists between said ball and said conductive surface.

8. The assembly according to claim 1, further including a terminal wire that is coupled to said conductive core of said elongated shaft within said handle.

9. A defibrillator assembly, comprising:
a control unit having a first terminal wire and a second terminal wire, wherein said control unit creates an electrical bias between said first terminal wire and said second terminal wire;
a conductive pad that is electrically interconnected with said control unit by said first terminal wire;
a paddle having a dielectric handle and a paddle head with a conductive surface thereon;
wherein a flexible shaft joins said handle to said paddle head, said flexible shaft having a conductive core protected by dielectric insulation; and
a pivot connection that joins said flexible shaft to said paddle head and enables said paddle head to move through a range of different orientations with respect to said flexible shaft wherein said pivot connection creates an electrical interconnection between said conductive core of said flexible shaft and said conductive surface of said paddle.

10. The assembly according to claim 9, wherein said flexible shaft is malleable and manually bendable into different configurations.

11. The assembly according to claim 9, wherein said paddle head has an oblong shape with a width and a length that is at least twice as long as said width.

12. The assembly according to claim 9, wherein said conductive surface on said paddle head is curved.

13. The assembly according to claim 9, further including at least one conductive element that extends through said paddle head from said conductive surface to said pivot connection, therein providing an electrical pathway from said pivot connection to said conductive surface.

14. The assembly according to claim 9, further including pivot nubs extending from said flexible shaft, wherein said pivot connection engages said pivot nubs and enables said paddle assembly to rotate about said pivot nubs through a range of motion.

15. The assembly according to claim 9, wherein said pivot connection is a ball joint having a conductive ball that is coupled to said flexible shaft.

16. The assembly according to claim 9, wherein an electrical pathway between said ball and said conductive surface.

17. The assembly according to claim 9, further including a terminal wire that is coupled to said conductive core of said flexible shaft within said handle.

* * * * *